United States Patent
Emadi et al.

(10) Patent No.: US 9,322,756 B2
(45) Date of Patent: Apr. 26, 2016

(54) NONDISPERSIVE INFRARED MICRO-OPTICS SENSOR FOR BLOOD ALCOHOL CONCENTRATION MEASUREMENTS

(71) Applicant: Maxim Integrated Products, Inc., San Jose, CA (US)

(72) Inventors: Arvin Emadi, Santa Clara, CA (US); Nicole D. Kerness, Menlo Park, CA (US); Christopher F. Edwards, Sunnyvale, CA (US)

(73) Assignee: Maxim Integrated Products, Inc., San Jose, CA (US)

(*) Notice: Subject to any disclaimer, the term of this patent is extended or adjusted under 35 U.S.C. 154(b) by 0 days.

(21) Appl. No.: 14/497,654

(22) Filed: Sep. 26, 2014

(65) Prior Publication Data

US 2015/0241347 A1 Aug. 27, 2015

Related U.S. Application Data

(60) Provisional application No. 61/942,919, filed on Feb. 21, 2014.

(51) Int. Cl.
| | |
|---|---|
| *G01N 21/00* | (2006.01) |
| *G01N 1/40* | (2006.01) |
| *G01N 21/59* | (2006.01) |
| *H04M 1/725* | (2006.01) |
| *G01N 21/01* | (2006.01) |
| *G01N 33/00* | (2006.01) |
| *G01N 33/49* | (2006.01) |
| *G01N 33/493* | (2006.01) |
| *G01N 33/497* | (2006.01) |

(52) U.S. Cl.
CPC ................ *G01N 1/40* (2013.01); *G01N 21/01* (2013.01); *G01N 21/59* (2013.01); *G01N 33/0036* (2013.01); *G01N 33/49* (2013.01); *G01N 33/493* (2013.01); *G01N 33/497* (2013.01); *G01N 33/4972* (2013.01); *H04M 1/72527* (2013.01)

(58) Field of Classification Search
CPC .................. G01N 33/4972; G05B 19/1425
USPC ................................. 250/338.1–338.5
See application file for complete search history.

(56) References Cited

U.S. PATENT DOCUMENTS

| | | | |
|---|---|---|---|
| 9,098,144 B1* | 8/2015 | Zeng et al. .................. 1/1 |
| 2003/0156290 A1* | 8/2003 | Colvin et al. ............ 356/411 |
| 2005/0261560 A1* | 11/2005 | Ridder et al. ............ 600/310 |
| 2007/0239992 A1* | 10/2007 | White et al. ............ 713/186 |
| 2008/0171924 A9 | 7/2008 | Ridder et al. |
| 2010/0160750 A1* | 6/2010 | White et al. ............ 600/322 |
| 2010/0266291 A1* | 10/2010 | Boffi et al. ............. 398/159 |
| 2011/0282167 A1 | 11/2011 | Ridder et al. |
| 2012/0055726 A1* | 3/2012 | Hannon .................. 180/272 |
| 2012/0197096 A1 | 8/2012 | Ridder et al. |

\* cited by examiner

*Primary Examiner* — Kiho Kim
(74) *Attorney, Agent, or Firm* — Advent, LLP (57) ABSTRACT

A nondispersive infrared (NDIR) micro-optics sensor package is described that includes one or more light sources, a photodetector, and control circuitry coupled to the one or more light sources to non-invasively measure blood alcohol concentration, such as without utilizing ex vivo bodily fluids for the measurements. Additionally, a mobile phone device configured to measure blood alcohol concentration is described that includes a mobile phone system and an NDIR micro-optics sensor package as disclosed above. Further, a process for measuring alcohol content within a subject is described.

14 Claims, 6 Drawing Sheets

NONDISPERSIVE INFRARED MICRO-OPTICS SENSOR FOR BLOOD ALCOHOL CONCENTRATION MEASUREMENTS

CROSS-REFERENCE TO RELATED APPLICATIONS

The present application claims the benefit under 35 U.S.C. §119(e) of U.S. Provisional Application Ser. No. 61/942,919, entitled NONDISPERSIVE INFRARED MICRO-OPTICS SENSOR FOR BLOOD ALCOHOL CONCENTRATION MEASUREMENTS, filed Feb. 21, 2014. U.S. Provisional Application Ser. No. 61/942,919 is hereby incorporated by reference in its entirety.

BACKGROUND

When alcohol, such as ethanol, is ingested, the alcohol is absorbed into the body's bloodstream and distributed throughout the body via the circulatory system, where the alcohol can be subsequently metabolized by or excreted from the body. A measure of blood alcohol concentration or content (BAC) can provide a metric for an individual's level of intoxication, where higher measurements typically project a higher level of physical/mental impairment or incapacitation as compared to lower measurements. Blood alcohol concentration can be determined through measurement of a bodily fluid, such as through analysis of expelled gas (e.g., breath analysis), blood, urine, and saliva.

SUMMARY

A nondispersive infrared (NDIR) micro-optics sensor package is described that includes one or more light sources, a photodetector, and control circuitry coupled to the one or more light sources to non-invasively measure blood alcohol concentration, such as without utilizing ex vivo bodily fluids for the measurements. Additionally, a mobile phone device configured to measure blood alcohol concentration is described that includes a mobile phone system and an NDIR micro-optics sensor package as disclosed above. Further, a process for measuring alcohol content within a subject is described.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

DRAWINGS

The detailed description is described with reference to the accompanying figures. The use of the same reference numbers in different instances in the description and the figures may indicate similar or identical items.

DETAILED DESCRIPTION

Overview

Current methods for measuring blood alcohol concentration can involve an ex vivo analysis of a bodily fluid, such as through an ex vivo analysis of expelled gas (e.g., breath analysis), blood, urine, and saliva. Such analysis of bodily fluids can be undesirable for efficiency, privacy, or other reasons. Other methods for measuring blood alcohol concentration can involve bulky equipment, such as blackbody radiators and Fourier Transform spectrometers, that is not configured for integration in mobile devices.

Accordingly, a nondispersive infrared (NDIR) micro-optics sensor package is described that includes a plurality of light sources (e.g., light-emitting diodes (LEDs)), a photodetector, and control circuitry coupled to the plurality of light sources to non-invasively measure blood alcohol concentration, such as without utilizing ex vivo bodily fluids for the measurements. Additionally, a mobile phone device configured to measure blood alcohol concentration is described that includes a mobile phone system and an NDIR micro-optics sensor package as disclosed above. In implementations, a process for measuring blood alcohol concentration includes emitting light from a plurality of light sources having differing wavelengths, sensing an electromagnetic absorption by one or more of ethanol and water at a plurality of wavenumbers with a photodetector, and correlating the sensed electromagnetic absorption by ethanol and water to determine blood alcohol concentration.

Example Implementations

Figure 1A:
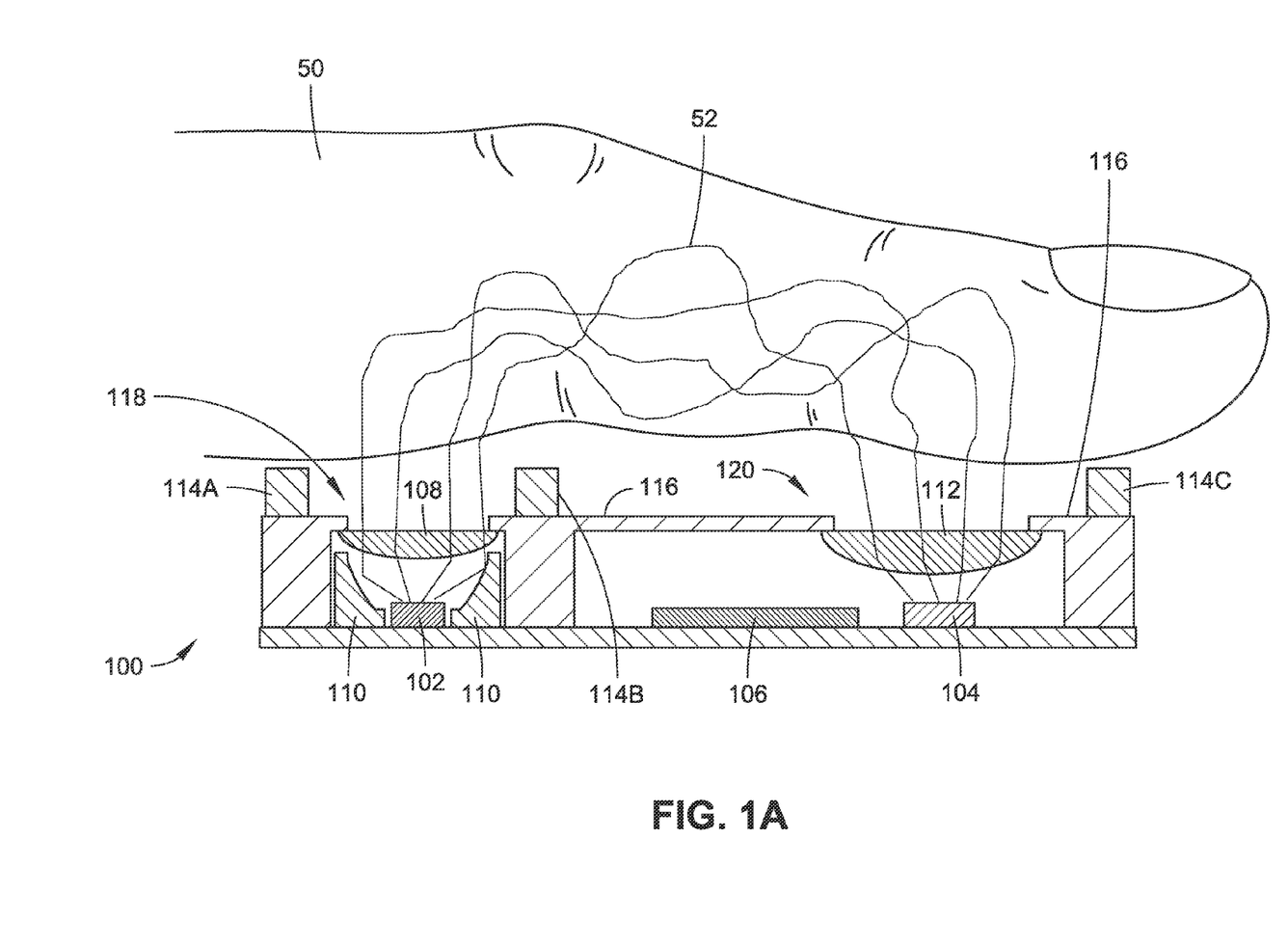
FIG. 1A is a diagrammatic side view illustrating an optics-based sensor for the measurement of blood alcohol concentration in accordance with example implementations of the present disclosure.

Referring to FIG. 1A, a mobile micro-optics sensor package 100 for the measurement of blood alcohol concentration is shown in accordance with example implementations of the present disclosure. In embodiments, the mobile micro-optics sensor package 100 is integrated with a mobile electronic device, such as a mobile phone (e.g., "smart" phone), a tablet, a computer, and so forth. As shown, the mobile micro-optics sensor package 100 includes a plurality of light sources 102, a photodetector 104, and control circuitry 106 operably coupled to the plurality of light sources 102 and the photodetector 104. In general operation, a user places a finger 50 over the mobile micro-optics sensor package 100, where the plurality of light sources 102 generate light directed into the finger. The light is scattered, absorbed, and reflected throughout the skin (such as along various paths 52), where the photodetector 104 measures light leaving the finger 50. The control circuitry 106 is configured to drive the plurality of light sources 102, to read/receive the output from the photodetector 104, and to process the received signal, such as through signal conditioning, whereby a digital output (e.g., of a blood alcohol concentration within the finger 50) can be provided from the mobile micro-optics sensor package 100. In implementations, the control circuitry 106 is an application-specific integrated circuit (ASIC) used to drive the components of the mobile micro-optics sensor package 100, provide low intensity signal detection and calibration, and so forth.

In implementations, the plurality of light sources 102 share a lens 108 configured to direct the light from the light sources 102 into the finger 50, although the light sources 102 can utilize individualized lens for one or more of the light sources 102. The lens 108 can include a downward curvature, an upward curvature, no curvature (e.g., a plain "window" configuration), and so forth. The lens 108 can be configured to condition (e.g., block, filter, focus, collimate, diffuse, etc.) electromagnetic radiation from the plurality of light sources 102 to the finger 50. The lens 108 can be positioned above one or more reflectors 110 (e.g., parabolic reflectors) configured to reflect light from the plurality of light sources 102 up to the lens 108. In an alternative implementation, the package 100 includes a metalized interior surface having a parabolic shape to reflect light from the plurality of light sources 102 up to the lens 108.

In embodiments, the light sources 102 may include one or more light emitting diodes (LED), one or more vertical-cavity surface-emitting lasers (VCSEL), and so forth. In one or more specific implementations, the plurality of light sources 102 include between two and fourth LEDs, each of which is configured to produce light in the near-IR spectral region. The output wavelengths of the LEDs can be selected based on spectral absorbance bands of ethanol and/or water. For example, in implementations, the LEDs can include output wavelengths having peaks of approximately 1.4 microns, 1.6 microns, 1.9 microns, 2.25 microns, and so forth. In implementations, the LEDs can have a full width half maximum (FWHM) bandwidth of from approximately 100 nanometers to 150 nanometers. The photodetector 104 can be a near-IR sensor, such as a III-V compound photodetector, a thermopile, a bolometer, and so forth configured to detect the output of light scattered from the finger 50. In implementations, a single photodetector 104 with a large area is used to receive as much light as possible from the finger 50. For example, the size of the photodetector 104 can range from 1 mm by 1 mm to 2.6 mm by 2.6 mm. Alternatively, a plurality of photodetectors are provided, where the outputs from each of the plurality of photodetectors are used to provide an indication of the total amount of light received. The photodetector 104 can be selected to detect light from particular electromagnetic spectrums, such as those that conform to the output wavelengths of the plurality of light sources 102. For example, in implementations, the photodetector 104 is configured to detect light having wavelengths from approximately 1.2 microns to 2.5 microns. The photodetector 104 can include an integrated lens 112 (e.g., a near-IR lens) configured to condition (e.g., block, filter, focus, collimate, diffuse, etc.) electromagnetic radiation leaving the finger 50 toward the photodetector 104. In implementations, the materials of the lens 112 can include one or more of glass, Silicon, Germanium, a near-IR transparent plastic, and so forth.

The mobile micro-optics sensor package 100 can include one or more baffles 114 (shown in FIG. 1A as 114A, 114B, 114C) projecting outward from a top surface 116 of the package 100. For example, in implementations, the package 100 includes a baffle 114B positioned between an output region 118 of the plurality of light sources 102 and the input region 120 of the photodetector 104. The baffle 114B can be configured to prevent cross-contamination of light from the plurality of light sources 102 to the photodetector 104, such that the light received by the photodetector 104 is that light which is scattered by the finger 50. The baffles 114 can also be configured to support the finger 50 above the mobile micro-optics sensor package 100, such as, for example, to avoid contact between the finger 50 and one or more of the lens 108, 112.

In implementations, the plurality of light sources 102 includes light sources in the near-IR spectral region. For example, the light sources 102 can include LEDs (e.g., two or three LEDs) with electromagnetic output having peaks at one or more ethanol absorption spectral regions, can include LEDS (e.g., one or two) with electromagnetic output having peaks at one or more water absorption spectral regions, can include LEDS (e.g., one or two) with electromagnetic output having peaks at absorption spectral regions for both ethanol and water, and so forth. In implementations, the light sources 102 include laser diodes with output wavelengths corresponding to one or more ethanol absorption spectral regions, to one or more water absorption spectral regions, to absorption spectral regions for both ethanol and water, and so forth. The control circuitry 106 can measure Blood Alcohol Concentration (BAC) by comparing signals received from each channel (e.g., particular wavelengths) and calibrating the measurements, described further herein.

Figure 1B:
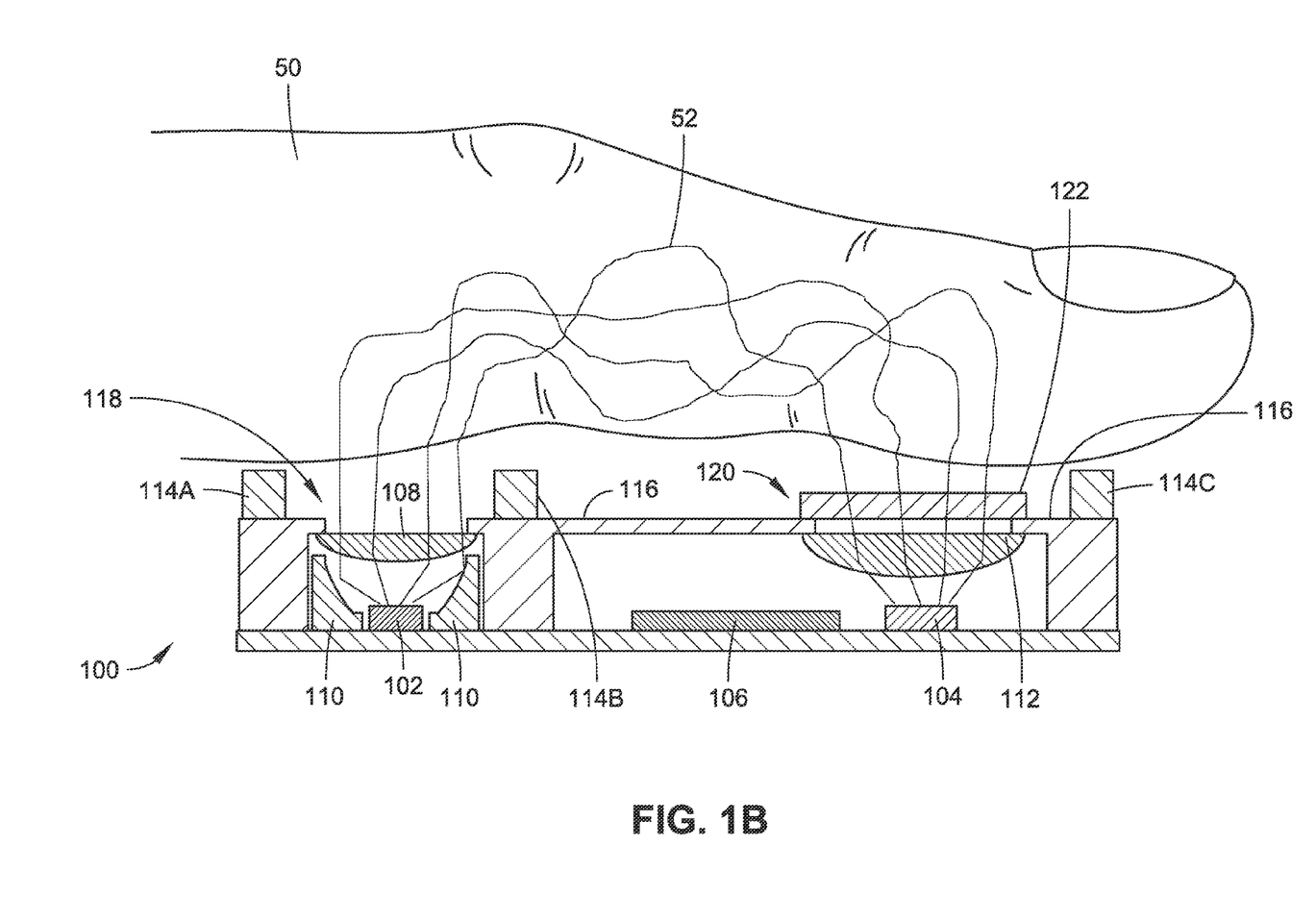
FIG. 1B is a diagrammatic side view illustrating an optics-based sensor for the measurement of blood alcohol concentration in accordance with example implementations of the present disclosure.

Referring to FIG. 1B, and example implementation of the mobile micro-optics sensor package 100 is provided. As shown, the mobile micro-optics sensor package 100 includes a filter 122 proximate to the photodetector 104, such that the output of light scattered from the finger 50 passes through the filter 122 prior to being received at the photodetector 104. While FIG. 1B shows the filter 122 supported by the top surface 116 located between above the lens 112 (i.e., between the finger 50 and the lens 112), it is noted that the filter 122 can be positioned in other configurations, including but not limited to, between the photodetector and 104 and the lens 112. The filter 122 is configured to filter light received from the output of light scattered from the finger 50 and to pass light in a limited spectrum or spectra of wavelengths to the photodetector 104. In implementations, the filter 122 is configured to incorporate one or more of an absorption filter, an interference filter, a flat pass filter, and so forth, configured to block particular wavelengths of light, while permitting passage of other wavelengths of light to the photodetector 104. For example, the filter 122 can include one or more filters configured to pass light having wavelengths of approximately 1.4 microns, 1.6 microns, 1.9 microns, 2.25 microns, which correspond to the wavelengths associated with the plurality of light sources 102 described with reference to FIG. 1A. In implementations, use of the filter 122 permits the light source 102 to include one or more broadband emitters, such that the filter 122 filters light received from the output of light scattered from the finger 50 and passes light in a limited spectrum or spectra of wavelengths to the photodetector 104. The one or more broadband emitters can be incorporated in combination with the plurality of light sources 102 at various emission spectra, can be incorporated to the exclusion of the plurality of light sources 102 at various emission spectra, and so forth.

Figure 2:
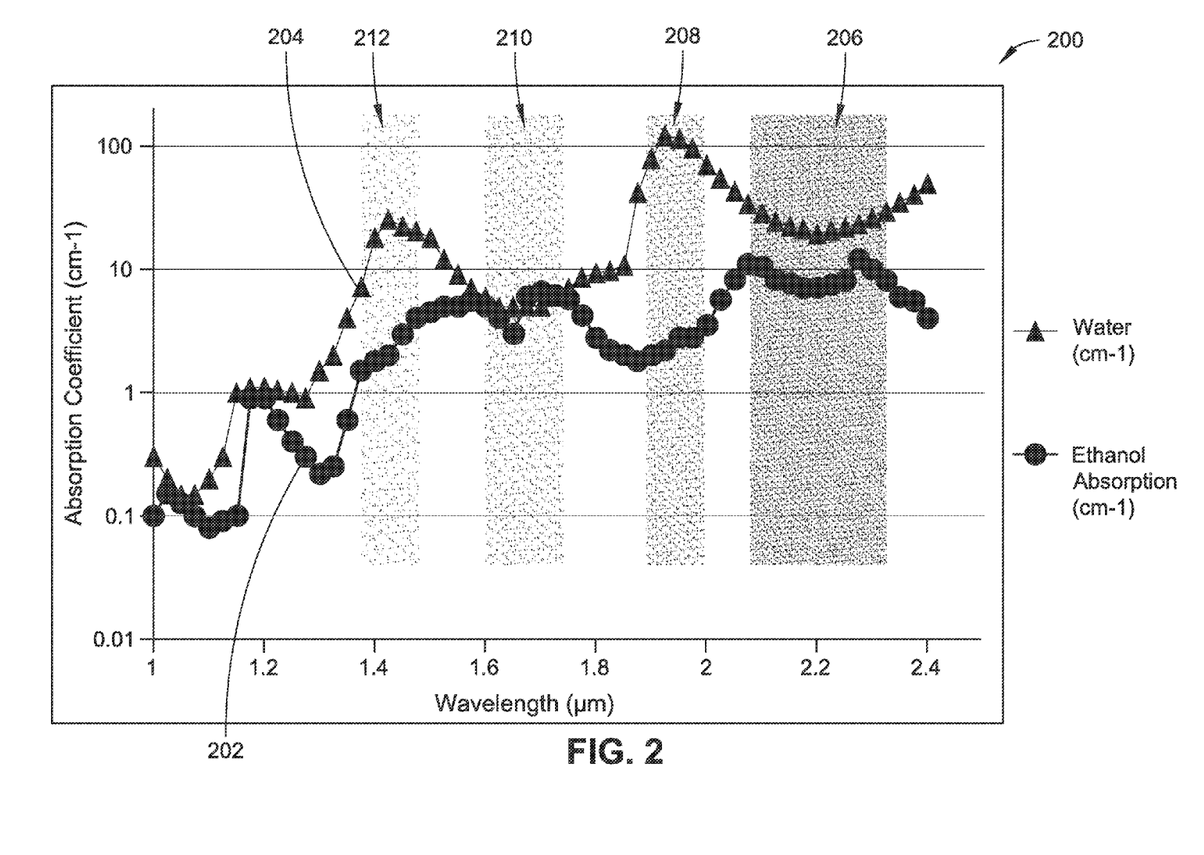
FIG. 2 is a spectroscopic diagram for ethanol and water showing absorbance at various wavelengths in accordance with example implementations of the present disclosure.

Referring now to FIG. 2, an example spectroscopic diagram 200 for ethanol and water showing absorbance at various wavelengths is shown in accordance with example implementations of the present disclosure. The diagram shows an example near-IR absorption spectrum of ethanol (the solid line indicated by 202) and of water (the dashed line indicated by 204). The example absorption spectrums of ethanol and water have indicated four wavelengths or wavelength bands, shown as 206, 208, 210, and 212. At 206, ethanol shows an absorption peak, whereas water has some absorption. When the photodetector 104 measures data at the wavelength(s) at 206, the signal can provide a strong indication of the presence of ethanol, while providing some indication of the presence of water. At 208, both ethanol and water show strong absorption peaks. When the photodetector 104 measures data at the wavelength(s) at 208, the signal can provide a strong indication of the presence of each of ethanol and water. At 210, neither ethanol nor water show absorption peaks. When the photodetector 104 measures data at the wavelength(s) at 210, the signal can provide data for signal corrections (such as for the positioning of the finger 50 on the mobile micro-optics sensor package 100), since the signal should indicate no peaks for ethanol or water. At 212, water shows an absorption peak, whereas ethanol has no discernable peak. When the photodetector 104 measures data at the wavelength(s) at 212, the signal can provide a strong indication of the presence of water, without significant interference from the presence of ethanol. Example processes for determining blood alcohol concentration are described below with respect to FIGS. 3 and 4.

Example Processes

Figure 3:
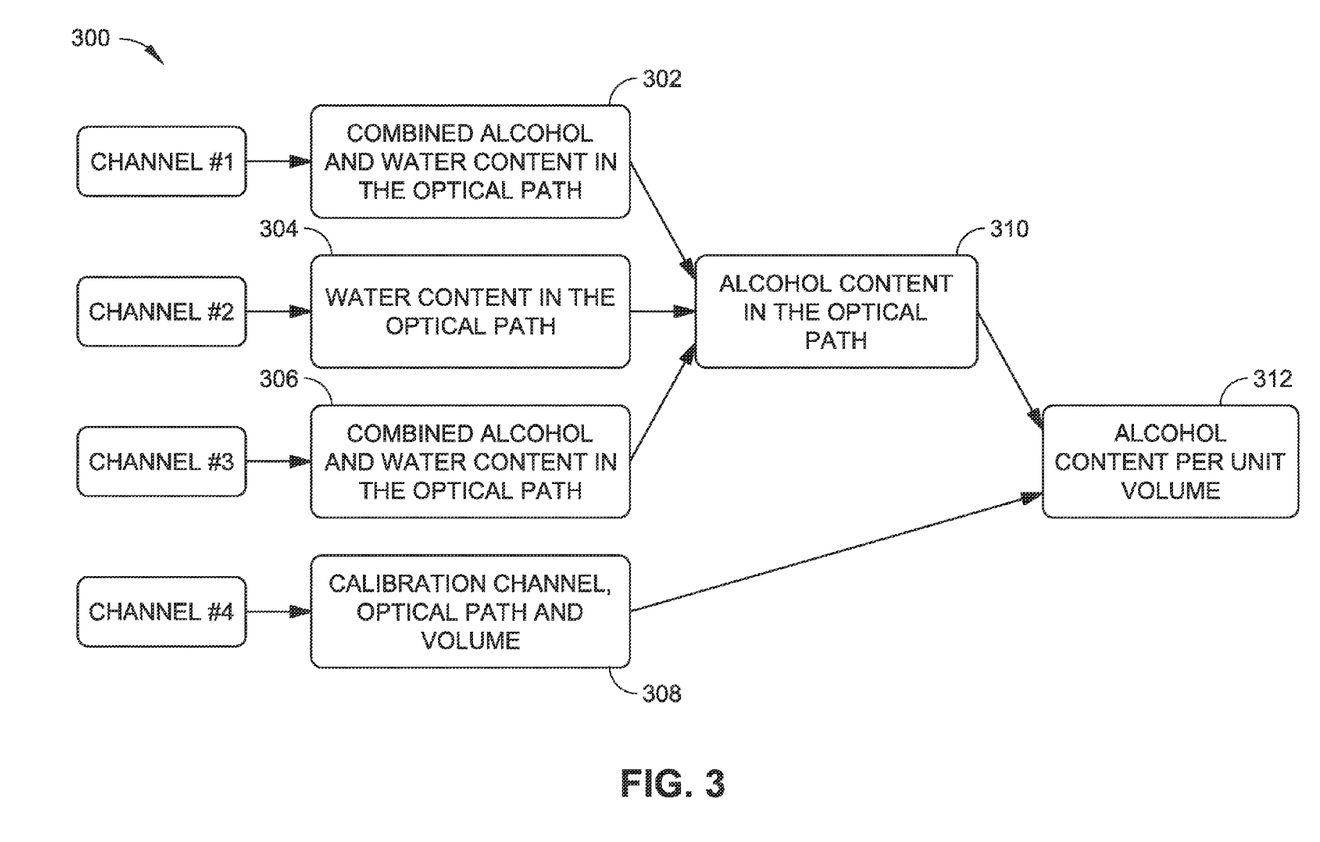
FIG. 3 is a flow diagram illustrating a process in an example implementation for utilizing an optics-based sensor for the measurement of blood alcohol concentration, such as the sensors shown in FIGS. 1A and 1B.

FIG. 3 provides a flow diagram 300 illustrating a process in an example implementation for utilizing an optics-based sensor for the measurement of blood alcohol concentration, such as the mobile micro-optics sensor package 100 shown in FIGS. 1A and 1B. As shown, four channels of signals are obtained (such as via photodetector 104), where each channel may correspond to the four wavelengths or wavelength bands, shown as 206, 208, 210, and 212 in FIG. 2. For example, channel #1 may correspond to 208, channel #2 may correspond to 212, channel #3 may correspond to 206, and channel #4 may correspond to 210. In implementations, the signal output of channel #1 may represent the combined alcohol and water content in the optical path (e.g., the path of the light from the plurality of light sources 102 through the finger 50, and out to the photodetector 104) (shown as 302), the signal output of channel #2 may represent the water content in the optical path (shown as 304), the signal output of channel #3 may represent the combined alcohol and water content in the optical path (shown as 306), and the signal output of channel #4 may represent a calibration channel for the optical path and for providing the volume of fluid (shown as 308). The combination of channels #1, #2, and #3 can provide the alcohol content along the optical path, but within an unknown volume of fluid (shown as 310). For example, the signal output of channel #2 can provide an indication of water concentration inside an unknown volume of fluid. With the water concentration from channel #2, alcohol concentration inside the same unknown volume can be calculated from channel #1. The signal output of channel #4 can be used to determine the volume of the unknown volume of fluid. The signal output from channel #3 can be used to account for scattering effects and relative absorption difference between water and alcohol, as well as the existence of various materials in the bloodstream/tissue that affect spectral transmission over the optical path. Accordingly, determining the alcohol content along the optical path from channels #1, #2, and #3 and by determining the volume of fluid along the optical path from channel #4, the alcohol content per unit volume can be calculated (shown as 312).

Figure 4:
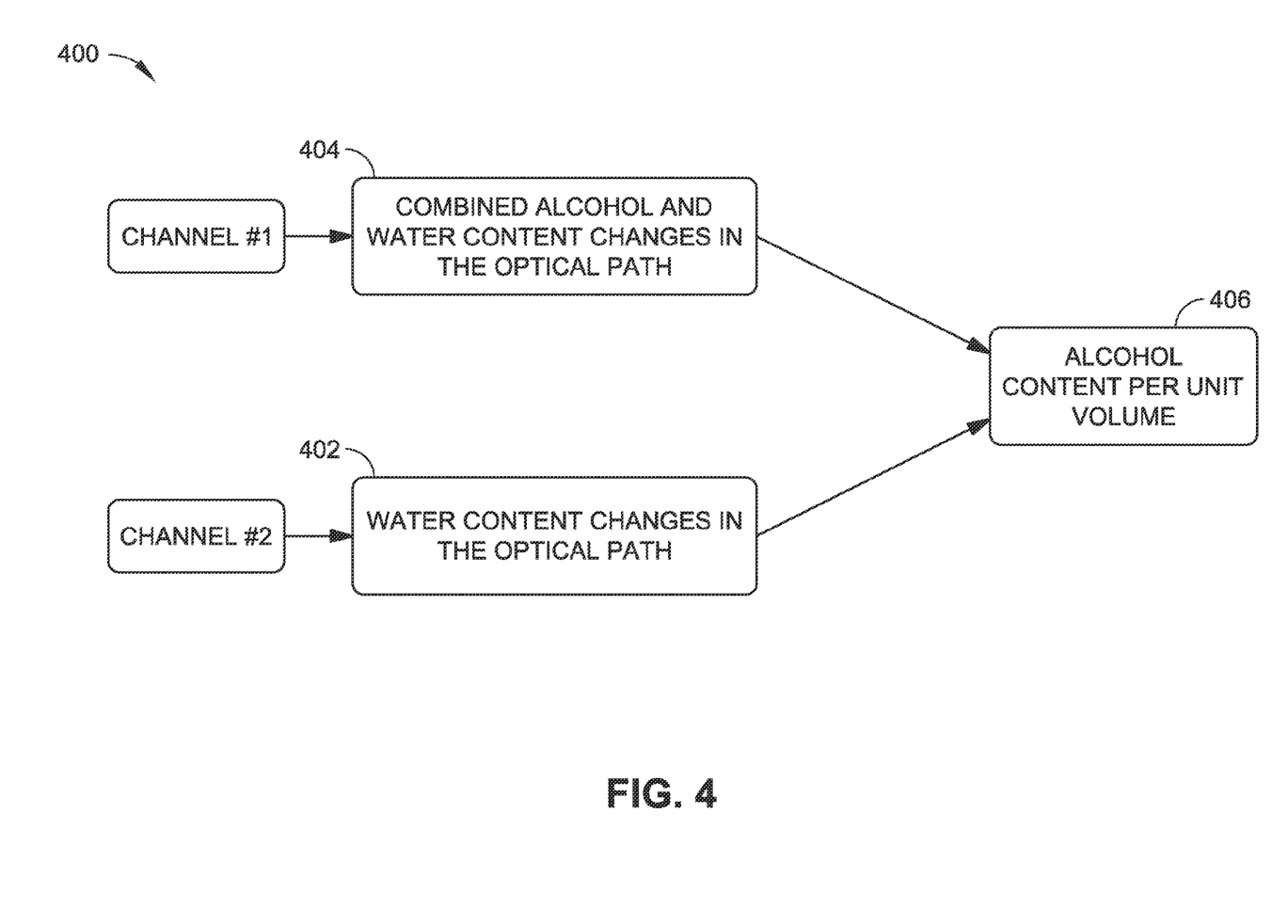
FIG. 4 is a flow diagram illustrating a process in an example implementation for utilizing an optics-based sensor for the measurement of blood alcohol concentration, such as the sensors shown in FIGS. 1A and 1B.
Figure 5:
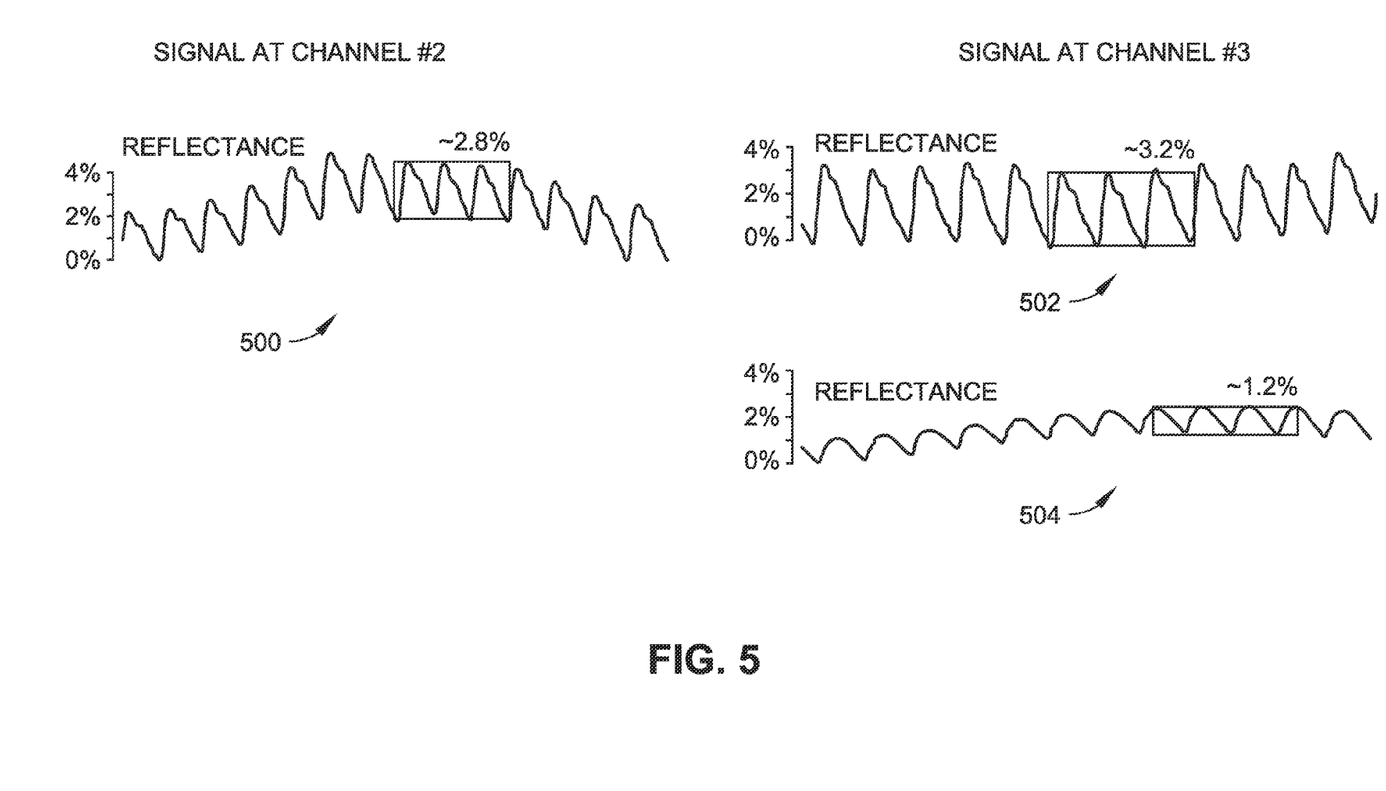
FIG. 5 is a chart indicating alternating current signal components measured at a photodetector in accordance with example implementations of the present disclosure.

FIG. 4 provides a flow diagram 400 illustrating a process in an example implementation for utilizing an optics-based sensor for the measurement of blood alcohol concentration, such as the mobile micro-optics sensor package 100 shown in FIGS. 1A and 1B. As shown, two channels of signals are obtained (such as via photodetector 104), where channel #1 can correspond to wavelength or wavelength band 206 or 208 in FIG. 2 and channel #2 can correspond to wavelength or wavelength band 212. For example, the signal output from channel #2 may include transient variations of signal (e.g., an alternating current (AC) component), caused by heart pulsations during the travel of light along the optical path, which can provide an indication of the water concentration changes in the skin during the pulsation (shown as 402). The signal output from channel #1 may include transient variations of signal (e.g., an AC component), caused by heart pulsations during the travel of light along the optical path, which can provide an indication of a combination of water and alcohol concentration changes in the skin during the pulsation (shown as 404). In implementations, the ratio of the two AC components (i.e., the AC components from channel #1 and channel #2) can be used to determine an alcohol concentration in the blood (shown as 406). For example, referring to FIG. 5, alternating current signal components measured at the photodetector 104 are shown. An alternating signal component for a first channel (e.g., a signal at channel #2) is shown as 500, whereas alternating signal components for a second channel (e.g., a signal at channel #3) are shown as 502 for a first period of time and 504 for a second period of time. Where a channel is configured to detect alcohol absorption, an AC-signal can provide information regarding the alcohol content, such as by a ratiometric analysis. For example, the alternating signal component for a first channel at 500 remains consistent over time within the 2.8% reflectance range, whereas the alternating signal component 502 remains within the 3.2% reflectance range during the first period of time, and then changes to a 1.2% reflectance range during the second period of time. The 2.0% reflectance range difference between the charts of 502 and 504 can be utilized to provide an indication regarding the alcohol content in an individual's system. By focusing on AC signal components, the measurement should not be affected by contamination of the surface of the skin of the finger, such as if alcohol or water were present on the finger 50, since the measurement of any alcohol or water on the skin surface would remain unchanged over time, thereby not affecting an AC component measurement.

CONCLUSION

Although the subject matter has been described in language specific to structural features and/or process operations, it is to be understood that the subject matter defined in the appended claims is not necessarily limited to the specific features or acts described above. Rather, the specific features and acts described above are disclosed as example forms of implementing the claims.

What is claimed is:

1. A mobile micro-optics sensor package for blood alcohol concentration measurements, comprising:
 a package substrate having an output region, an input region, and a baffle positioned between the output region and the input region;
 a light source coupled to the package substrate and configured to generate light having a plurality of wavelengths, at least one of the plurality of wavelengths corresponding to a peak spectral absorption of ethanol and water, and at least one of the plurality of wavelengths corresponding to a peak spectral absorption of water, the light source configured to direct the light from the light source through the output region;

a photodetector coupled to the package substrate and configured to receive at least a portion of the light having the plurality of wavelengths through the input region and to generate one or more alternating current signal outputs in response thereto; and control circuitry coupled to the light source and the photodetector, the control circuitry configured to detect and calibrate the one or more alternating current signal outputs from the photodetector to determine a blood alcohol concentration based on spectral data associated with the wavelengths corresponding to a peak spectral absorption of ethanol and water and with the wavelengths corresponding to a peak spectral absorption of water and based on a detected change in reflectance range of the one or more alternating current signal outputs between a first reflectance range at a first time period and a second reflectance range at a second time period.

2. The mobile micro-optics sensor package for blood alcohol concentration measurements of claim 1, wherein the light source includes a plurality of light sources, each of the plurality of light sources configured to generate light having a different spectrum of wavelengths.

3. The mobile micro-optics sensor package for blood alcohol concentration measurements of claim 2, wherein the plurality of light sources includes a light source configured to generate light having a peak of approximately 1.4 microns, a light source configured to generate light having a peak of approximately 1.6 microns, a light source configured to generate light having a peak of approximately 1.9 microns, and a light source configured to generate light having a peak of approximately 2.25 microns.

4. The mobile micro-optics sensor package for blood alcohol concentration measurements of claim 1, wherein the light source includes a light emitting diode.

5. The mobile micro-optics sensor package for blood alcohol concentration measurements of claim 1, wherein the light source includes a laser diode.

6. The mobile micro-optics sensor package for blood alcohol concentration measurements of claim 1, further including a filter configured to receive at least a portion of the light generated by the light source and to block a portion of the light and to pass light having wavelengths corresponding to a peak spectral absorption of ethanol and water and having wavelengths corresponding to a peak spectral absorption of water.

7. A mobile phone device comprising:
a mobile phone system; and
a mobile micro-optics sensor package integrated into the mobile phone system, including:
a package substrate having an output region, an input region, and a baffle positioned between the output region and the input region;
a light source coupled to the package substrate and configured to generate light having a plurality of wavelengths, at least one of the plurality of wavelengths corresponding to a peak spectral absorption of ethanol and water, and at least one of the plurality of wavelengths corresponding to a peak spectral absorption of water, the light source configured to direct the light from the light source through the output region;
a photodetector coupled to the package substrate and configured to receive at least a portion of the light having the plurality of wavelengths through the input region and to generate one or more alternating current signal outputs in response thereto; and
control circuitry coupled to the light source and the photodetector, the control circuitry configured to detect and calibrate the one or more alternating current signal outputs from the photodetector to determine a blood alcohol concentration based on spectral data associated with the wavelengths corresponding to a peak spectral absorption of ethanol and water and with the wavelengths corresponding to a peak spectral absorption of water and based on a detected change in reflectance range of the one or more alternating current signal outputs between a first reflectance range at a first time period and a second reflectance range at a second time period.

8. The mobile phone device of claim 7, wherein the light source includes a plurality of light sources, each of the plurality of light sources configured to generate light having a different spectrum of wavelengths.

9. The mobile phone device of claim 8, wherein the plurality of light sources includes a light source configured to generate light having a peak of approximately 1.4 microns, a light source configured to generate light having a peak of approximately 1.6 microns, a light source configured to generate light having a peak of approximately 1.9 microns, and a light source configured to generate light having a peak of approximately 2.25 microns.

10. The mobile phone device of claim 7, wherein the light source includes a light emitting diode.

11. The mobile phone device of claim 7, wherein the light source includes a laser diode.

12. The mobile phone device of claim 7, further including a filter configured to receive at least a portion of the light generated by the light source and to block a portion of the light and to pass light having wavelengths corresponding to a peak spectral absorption of ethanol and water and having wavelengths corresponding to a peak spectral absorption of water.

13. A process for measuring alcohol content within a subject, comprising:
emitting light from a light source, the light having a plurality of wavelengths, at least one of the plurality of wavelengths corresponding to a peak spectral absorption of ethanol and water, at least one of the plurality of wavelengths corresponding to a peak spectral absorption of water, and at least one of the plurality of wavelengths having a peak of approximately 1.6 microns corresponding to a calibration channel for an optical path of the light through the subject;
sensing an electromagnetic absorption of at least a portion of the light by water and by a combination of water and ethanol at the plurality of wavelengths corresponding to a peak spectral absorption of ethanol and water and to a peak spectral absorption of water; and
correlating the sensed electromagnetic absorption by comparing a first reflectance range of one or more of alternating current signal components corresponding to electromagnetic absorption at the plurality of wavelengths corresponding to a peak spectral absorption of ethanol and water and alternating current signal components corresponding to electromagnetic absorption at the plurality of wavelengths corresponding to a peak spectral absorption of water at a first time period with a second reflectance range of the one or more of alternating current signal components corresponding to electromagnetic absorption at the plurality of wavelengths corresponding to a peak spectral absorption of ethanol and water and alternating current signal components corresponding to electromagnetic absorption at the plurality of wavelengths corresponding to a peak spectral absorption of water at a second time period to determine an alcohol content within a subject.

14. The process of claim 13, wherein emitting light from a light source further includes emitting light having a peak of approximately 1.4 microns, emitting light having a peak of approximately 1.9 microns, and emitting light having a peak of approximately 2.25 microns.

\* \* \* \* \*